United States Patent [19]

Boddie, Jr. et al.

[11] Patent Number: 4,674,481
[45] Date of Patent: Jun. 23, 1987

[54] RF ELECTROMAGNETIC FIELD GENERATION APPARATUS FOR REGIONALLY-FOCUSED HYPERTHERMIA

[75] Inventors: Arthur W. Boddie, Jr.; James W. Frazer, both of Houston, Tex.; William S. Yamanashi, Jenks, Okla.

[73] Assignee: Board of Regents, The University of Texas System, Austin, Tex.

[21] Appl. No.: 546,917

[22] Filed: Oct. 31, 1983

[51] Int. Cl.⁴ .............................................. A61B 17/52
[52] U.S. Cl. ..................................... 128/1.3; 128/804
[58] Field of Search ................ 128/1.3, 734, 799, 800, 128/804, 783–786; 219/6.5

[56] References Cited

U.S. PATENT DOCUMENTS

| | | | |
|---|---|---|---|
| 4,121,592 | 10/1978 | Whalley | 128/800 |
| 4,230,129 | 10/1980 | LeVeen | 128/804 |
| 4,237,898 | 12/1980 | Whalley | 128/800 |
| 4,252,130 | 2/1981 | LePrist | 128/734 |
| 4,285,346 | 8/1981 | Armitage | 128/804 |
| 4,292,980 | 10/1981 | Suzuki | 128/783 |
| 4,306,568 | 12/1981 | Jorre | 128/734 |
| 4,325,261 | 4/1982 | Harrison | 128/804 |
| 4,346,715 | 8/1982 | Gammrell | 128/804 |
| 4,350,168 | 9/1982 | Chable et al. | 128/798 |
| 4,448,198 | 5/1984 | Turner | 128/804 |

FOREIGN PATENT DOCUMENTS

| | | | |
|---|---|---|---|
| 2,913,430 | 10/1980 | Fed. Rep. of Germany | 128/804 |
| 8301902 | 6/1983 | PCT Int'l Appl. | 128/804 |
| 0971351 | 11/1982 | U.S.S.R. | 128/1.3 |

OTHER PUBLICATIONS

NBS Technical Note 652; Development and Construction of an Electromagnetic Near-Field Synthesizer; Frank M. Greene; May 1974.

*Primary Examiner*—Edward M. Coven
*Assistant Examiner*—Max F. Hindenburg
*Attorney, Agent, or Firm*—Arnold, White & Durkee

[57] ABSTRACT

A hyperthermia treatment device comprises paired multiple feed inductor rings positioned between two capacitor plates, for producing a tuned radiofrequency electromagnetic field. The spatial orientation of the elements and/or the phase of the current flowing through them is variable. Change in the spatial orientation and phase of the inductor rings produce asymmetric magnetic field patterns resulting in the development of asymmetric eddy current patterns orthogonal to the magnetic lines of force. The eddy current patterns are further focused by spatial orientation and phase adjustment of the capacitor plates. A movable grounding point is utilized to further focus induced eddy currents. The device is capable of producing focal hyperthermia at depth to heat specific volumes.

25 Claims, 21 Drawing Figures

RF ELECTROMAGNETIC FIELD GENERATION APPARATUS FOR REGIONALLY-FOCUSED HYPERTHERMIA

FIELD OF THE INVENTION

The present invention relates to devices for producing controlled electromagnetic fields in the radiofrequency range for generation of hyperthermia.

BACKGROUND OF THE INVENTION

Regional hyperthermia is a promising new modality of anticancer therapy; but since hyperthermia can also damage normal tissues, further progress in the field requires development of devices capable of focusing heat into tumors or tumor bearing organs without damage to adjacent structures. While considerable progress has been made in the focal heating of tumors located at or near the skin surface, the focal heating of deeply seated tumors has been a more elusive goal. This problem results largely from the fact that electromagnetic radiation in that portion of the frequency spectrum which has deep penetrance in biologic tissues does not have quasi-optic properties while higher frequency EM radiation has quasi-optic properties but limited penetrance.

Therefore, well-focused hyperthermia at depths of more than 5-6 cm below the skin probably requires at least partial use of invasive methods because of constraints resulting from the physical interactions of electromagnetic waves and biologic systems. Safety considerations suggest that invasive devices with sharply focused heating patterns may be preferred for deep hyperthermia. Sharply focused heating also permits temperature monitoring using relatively few invasive temperature probes.

Currently used invasive methods, such as interstitial antennae or RF electrodes designed to accomplish focal heating of surface tumors, have several limitations in regard to heating deeply seated lesions. In the case of the interstitial antenna, the depth of insertion, which depends upon the length of the antenna, is not arbitrarily variable, since for optimum efficiency the antenna length should be some multiple of the incident wavelength. Also, the size of the heat deposition pattern in the vicinity of the antenna tip is significantly limited due to the characteristic interaction of the antenna and the medium, and this is not easily varied. In the case of RF electrodes, the current paths are dictated by the locations of the source and the sink electrodes and quite often require several electrodes to conform to the approximate contour of the desired heating volume (tumor). The use of multiple electrodes increases the risk of bleeding and tumor re-implantation.

SUMMARY OF THE INVENTION

The present invention provides apparatus for producing precisely controlled electromagnetic fields in the radiofrequency range for generation of regionally-focused hyperthermia. Moreover, the present invention provides for the generation of regionally-focused hyperthermia by producing precisely controlled electromagnetic fields that penetrate below the surface of an irradiated body. That is, the hyperthermia treatment device of the present invention is capable of producing focal hyperthermia at depth. Accordingly, the apparatus appears useful in the treatment of cancer by reason of its ability to permit focal heating of deeply seated tumors without damage to adjacent structures.

To produce regionally-focused hyperthermia at depth within a body, a radiofrequency magnetic field generator producing an asymmetrical magnetic field gradient in a horizontal plane is used. The alternating magnetic field gradient which is established in turn induces an eddy current gradient in a body within the field. A radiofrequency electric field generator is used to cancel certain of the induced eddy currents, thereby producing sharply focused magnetic field eddy currents.

The ability to produce asymmetrical magnetic field gradients is attained by the use of paired inductor rings. Manipulation of the spatial orientation of the inductor rings and manipulation of the phase of the current flowing through them produces a resultant magnetic field that can be made asymmetric. However, when the inductor rings are positioned in a Helmholtz configuration, the resultant magnetic field in the midplane between the rings has a symmetrical bell-shaped distribution with the maximum intensity in the center of the plane. Rotation of the inductor rings into a wedged configuration produces an asymmetrical field distribution in the midplane with the point of maximum intensity shifted off-center to the region where the rings are closer together.

The radiofrequency electric field generator is suitably realized through the use of parallel capacitor plates. With horizontal capacitor plates, the paired inductor rings are disposed between the capacitor plates and are vertically adjustable within the space between the plates.

Induced eddy currents are further focused by use of a movable grounding point disposed within the field of the magnetic field generator. The movable grounding point permits more precise focusing of eddy currents by taking advantage of voltage developed in objects within the field relative to ground and channeling the induced eddy currents along desired paths.

Further in accordance with the present invention the grounding point is suitably implemented as an invasive ground probe. That is, the grounding point is established at a location internally of the body to be heated. A suitable ground probe comprises an electrically-conductive rod having an insulating sheath thereover which exposes the tip end.

Another aspect of the invention relating to the grounding point element is the use of a current flow monitoring device to monitor the current flowing through the ground point. Ground point current monitoring is useful in tuning of the electromagnetic field generating elements of the device.

Further in accordance with the invention, combinations of more than one ground probe can be utilized. For example, two alternately switched ground probes can be utilized. Another grounding point arrangement contemplated by the present invention is the use of a grounded invasive probe in combination with one or more switched ground plates disposed externally of the body to be heated. Yet another grounding point arrangement contemplated by the invention is the use of a grounded plate and two switched grounding plates, all of which are disposed externally of the body to be heated. The external plates may suitably be applied externally to the sides of a body to be heated.

BRIEF DESCRIPTION OF THE DRAWINGS

A written description setting forth the best mode presently known for carrying out the present invention, and of the manner of implementing and using it, is provided by the following detailed description of an illustrative embodiment shown in the attached drawing figures wherein.

DETAILED DESCRIPTION OF AN ILLUSTRATIVE EMBODIMENT

Figure 1:
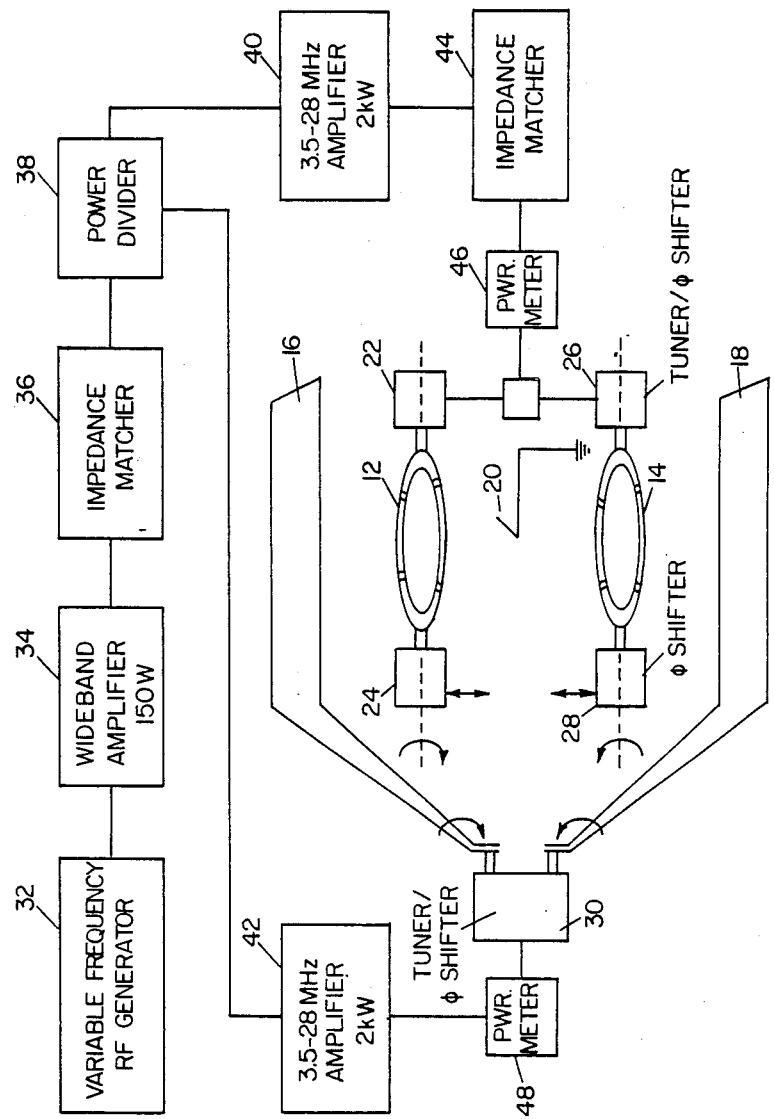
FIG. 1 is a block diagram of a hyperthermic treatment device in accordance with the present invention.

Referring first to FIG. 1, there is presented a block diagram of a hyperthermic treatment device in accordance with the present invention. The device includes an RF magnetic field generator comprising paired inductors 12 and 14 positioned between capacitor plates 16 and 18 which comprise an RF electric field generator. Additionally, a movable grounding point 20 is included. Each inductor ring is individually tuned, and the phase of each is separately adjusted by matching networks associated therewith. As indicated in FIG. 1, inductor ring 12 is provided with tuner/phase shifter networks 22 and 24 and inductor ring 14 is provided with tuner/phase shifter networks 26 and 28. Similarly, capacitor plates 16 and 18 can be tuned and the phase adjusted by tuner/phase shifter network 30. Finally, inductor rings 12 and 14 are vertically and rotationally adjustable. Capacitor plates 16 and 18 are also spatially adjustable.

The inductive and capacitive elements of the device are powered by a variable frequency RF generator 32, which may suitably be a MCL 15122 cavity frequency generator available from MCL, Inc., LaGrange, Ill. The signal from generator 32 is amplified by a wideband amplifier 34, such as a Boomer 150 watt amplifier available from V.J. Products of Pasadena, Tex. The amplified RF signal is routed through an impedance matcher 36 and split by a power divider network 38 comprising an ENI Model PML 100-2. The RF signal is split to drive amplifiers 40 and 42. These amplifiers are suitably ETO Alpha Model 76A, 1500 watt linear amplifiers available from Erhorn Technological Operations, Inc. of Canon City, Colo. The output of amplifier 40 is routed through an impedance matcher 44 and then supplied to inductor rings 12 and 14. The applied power is monitored by power meter 46 such as a Bird 2100 series directional power meter. Similarly, the output of amplifier 42 is applied to the capacitor element and the applied power is monitored by power meter 48. Preferably, the resonant frequency of the inductive and capacitive components of the present device is variable over a 3-50 MHz frequency range; and, the preferred range is 13-20 MHz.

Figure 2:
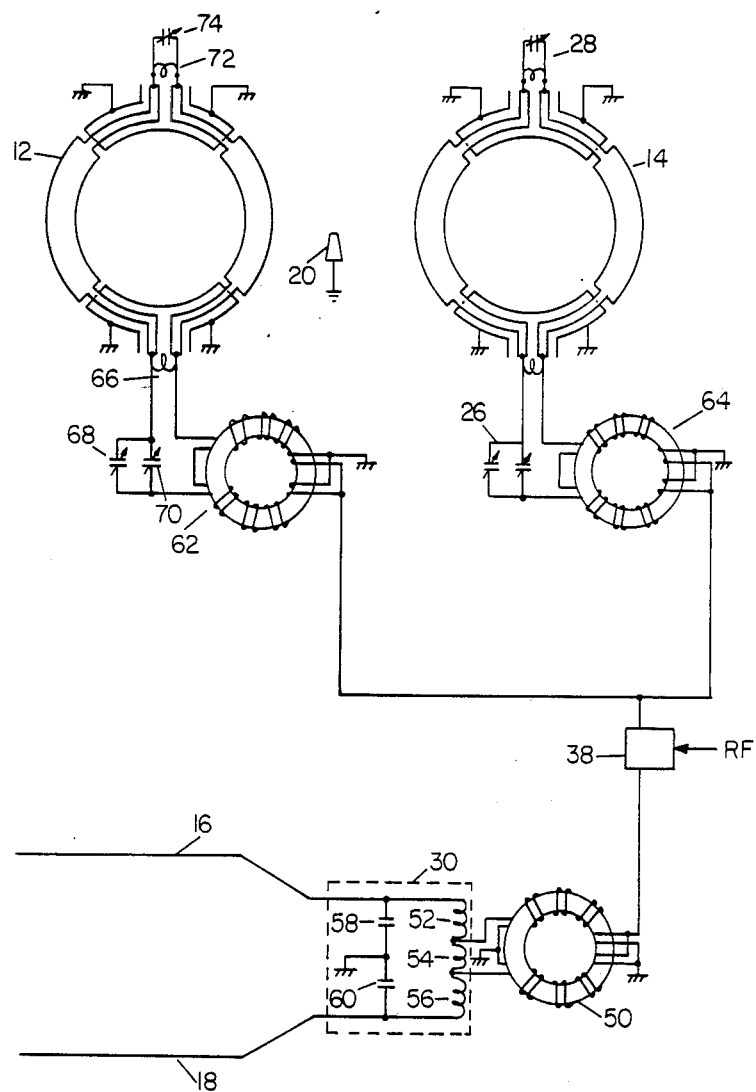
FIG. 2 is a schematic diagram for the device of FIG. 1.

Referring now to FIG. 2, an electrical schematic diagram is shown for the primary components of the device shown in FIG. 1. Specifically, the output of power divider 38 is applied to a toroidal balun transformer 50. The structure of transformer 50 is preferably in accordance with that described in NBS Technical Note 652, "Development and Construction of an Electromagnetic Near-Field Synthesizer," p. 11 (May 1974) which is hereby incorporated by reference.

The capacitor plate tuner/phase shifter network 30 includes inductors 52, 54 and 56 together with variable capacitors 58 and 60. The parallel capacitor plates 16 and 18 are tuned to resonance at the desired operating frequency by the balanced inductance provided by the inductors. Each vacuum capacitor has a range of adjustment from 6.5 to 50 pF and facilitates tuning. The input impedance is determined by the value selected for inductor 54 so that the reactance $X_L = 300$ ohms for the selected frequency. The network is preferably housed in an aluminum box. The size of the housing is dictated by the size of the tuning coils, and preferably a small fan is used to exhaust air from a vent in the enclosure to facilitate cooling the inductors.

Also, the balun transformer and inductors should be cooled by ethylene glycol continuously circulated through an arrangement of interconnected tubes.

Each capacitor plate is square and approximately 75 cm on each side. An RF driving power between 150 and 300 watts is required over the frequency range of 10–30 MHz to produce an electric field strength of 5000 volts per meter between the plates.

The other signal from power divider 38 is applied to upper inductor ring 12 and lower inductor ring 14 through respective balun transformers 62 and 64. These transformers are identical to transformer 50. Each of the inductor rings in the RF magnetic-field generator comprises a single-turn inductor having an inside diameter of 50 cm. The inductor ring is preferably formed from copper tubing having an outside diameter of 1⅜ inches and a wall thickness of 1/16 inch. The inductor has a low-frequency inductance of 0.921 microhenry. Inductor rings 12 and 14 are suitably constructed in accordance with the loop inductor described in National Bureau of Standards Technical Note 652, "Development and Construction of an Electromagnetic Near-Field Synthesizer," (May 1974). Further, each inductor ring is water-cooled by circulation therethrough of a coolant such as ethylene glycol.

The tuner/phase shifter network 22 for upper inductor ring 12 and network 26 for lower inductor ring 14 are identical. As shown in FIG. 2, network 22 comprises a combination of inductor 56 and vacuum variable capacitors 68, 70. Capacitor 68 provides for coarse tuning, while capacitor 70 provides for fine tuning. Suitably, the range of adjustment for capacitor 68 is from 100 to 1000 pF, and the range of adjustment for capacitor 70 is 10 to 100 pF. The value for inductor 56 is preferably 0.9 microhenries.

Phase shift network 24 for upper inductor ring 12 and phase shift network 28 for lower inductor ring 14 are also identical. As shown, network 24 includes an inductor 72 and variable capacitor 74. Inductor 72 preferably has a value of 10 microhenries, and capacitor 74 is variable over a range of adjustment from 10 to 1000 pF.

Figure 3:
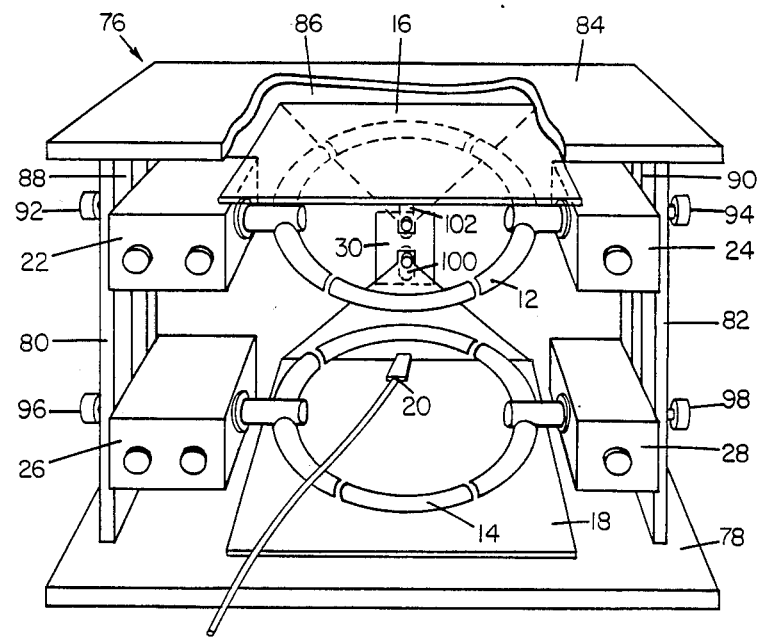
FIG. 3 is a perspective view of a mechanical layout for the elements shown in the diagram of FIG. 2.

In FIG. 3, there is presented a mechanical layout for the elements of the RF magnetic-field generator and the RF electric-field generator and the position adjustable ground plane. Generally speaking, the upper and lower inductor rings and the capacitor plates are mounted in a frame 76. In the layout shown in FIG. 3, frame 76 includes a base 78, sidewalls 80 and 82, a top cover 84, and backwall 86. The material of which frame 76 is constructed is, of course, non-metallic.

As indicated in the layout of FIG. 3, capacitor plates 16 and 18 are mounted to backwall 86. Also, the housing containing tuner/phase shifter network 30 is also mounted to the backwall 86. Both upper and lower inductor rings and their associated tuner/phase shifter network housings are supported by sidewalls 80 and 82. Further, the inductor rings are vertically adjustable within tracks 88 and 90 in the sidewalls. Rotational adjustment of inductor ring 12 is provided by knobs 92 and 94. Similarly, rotational adjustment of lower ring 14 is provided by knobs 96 and 98.

Capacitor plates 16 and 18 are vertically adjustable within slotted tracks opening 100 and 102 in backwall 86. Also, capacitor plates 16 and 18 are tiltable within frame 76.

Figure 4:
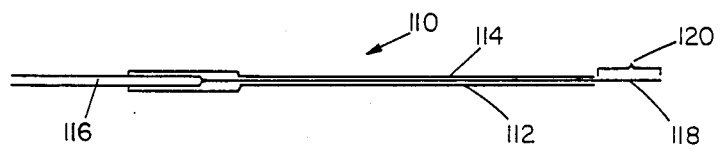
FIG. 4 is a diagram of a ground probe for use in the device of FIG. 1.

Referring to FIG. 4, there is diagrammed a probe structure for providing an invasive grounding point. The probe 110 comprises a stainless steel rod 112 with an insulating sheath 114. Attached to rod 112 is a clip 116 for connecting to a ground cable. The diameter of rod 112 is preferably about 1 millimeter. Also, a sharpened tip 118 is provided to facilitate percutaneous introductions. The insulating sheath material is preferably polyethylene in a thickness that establishes the outside diameter of the probe structure to about 1.5 millimeters. Further, the insulating sheath is preferably made longitudinally movable to permit adjustment of the length of the conducting tip portion 120 of the probe.

Figure 5:
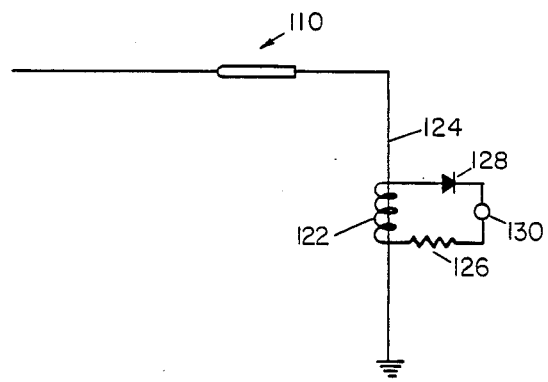
FIG. 5 is a schematic diagram of apparatus for monitoring ground current through the ground probe.

The magnitude of eddy current induced by the $\overline{H}$ component of the applied RF field or produced by capacitive coupling with the E field, which subsequently passes through the ground point as ground current, is monitored by apparatus shown in FIG. 5. This apparatus includes a pick-up coil 122 placed over the outside of the insulator of the ground cable 124 connected to probe 110. Coil 122 is connected in series with a current-limiting resistor 126 and diode 128. A meter 130 is connected across the circuit to provide a readout of ground current. It has been found that observed ground current has a linear relationship with the rate of heating in the initial portion of a heating curve. Accordingly, ground current monitoring of initial heat rise can be used as an aid in tuning the inductive and capacitive elements when a ground probe is used.

Figure 6:
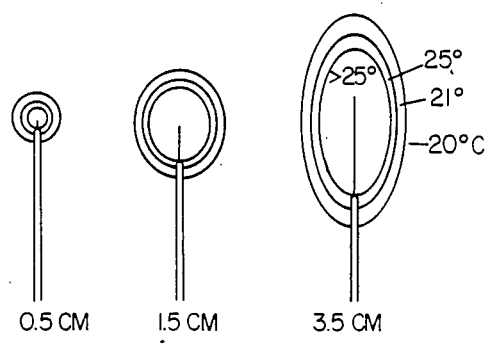
FIG. 6 presents isotherm patterns illustrating the effect of varying the length of the exposed tip of the ground probe.

In FIG. 6, there are presented isotherm patterns obtained for a single ground probe as the length of the exposed tip is varied from 0.5 cm to 1.5 cm to 3.5 cm.

To increase the volume or alter the distribution that can be heated with the use of grounding elements, more than one invasive ground probe can be used. For example, in FIG. 7 there is shown the use of two switched ground probes. Specifically, shown are upper and lower inductor rings 12 and 14 and upper and lower capacitor plates 16 and 18. A phantom body 150 to be heated has two invasive ground probes 130 and 140. Grounding of the probes is through switch 160 which provides for alternate grounding of one of the two probes.

Figure 8:
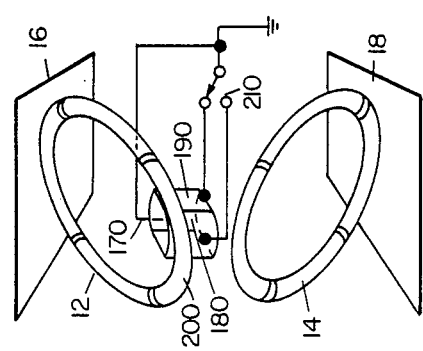
FIG. 8 is a diagram showing the use of an invasive ground probe in combination with two external grounding plates.

Another arrangement of grounding elements to increase the volume that can be heated comprises the use of an invasive ground probe in combination with external ground planes. Such an arrangement is shown in FIG. 8 wherein a ground probe 170 is centrally located in a phantom body 180 and two switched grounding plates 190 and 200 are applied externally to the vertical sides of body 180. The probe is continuously grounded, but plates 190 and 200 are alternately grounded through switch 210.

Figure 9:
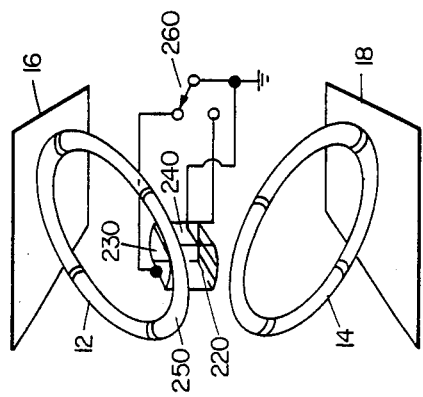
FIG. 9 is a diagram showing the use of one external constant grounding plate and two switched external grounding plates.

Yet another grounding arrangement is shown in FIG. 9. In this arrangement, one constantly-grounded grounding plate 220 is located at the external bottom surface of a body 230. Located externally and applied to the vertical sides of body 230 are two grounding plates 240 and 250, which are alternately connected to ground through switch 260.

Figure 7:
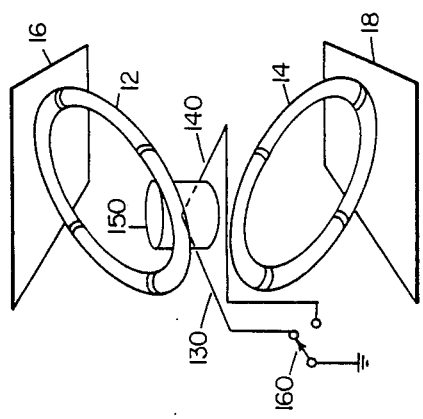
FIG. 7 is a diagram showing the use of two invasive ground probes.
Figure 12:
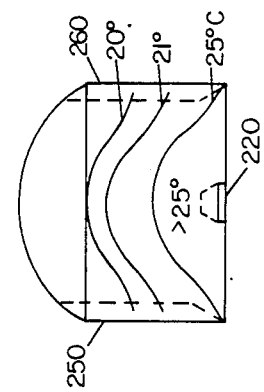
FIG. 12 is a diagram of the isotherm heating pattern for the ground point arrangement shown in FIG. 9.
Figure 11:
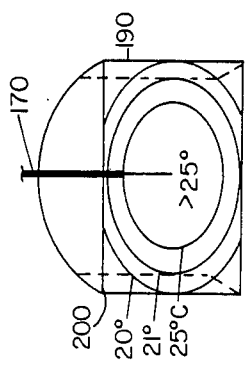
FIG. 11 is a diagram of the isotherm heating pattern for the ground point arrangement shown in FIG. 8.
Figure 10:
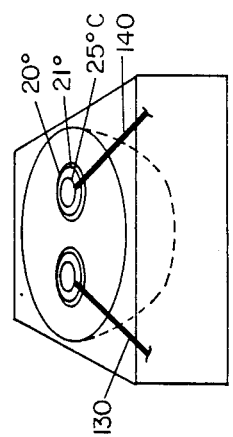
FIG. 10 is a diagram of the isotherm heating pattern for the ground point arrangement shown in FIG. 7.

In FIGS. 10, 11 and 12, there are presented isotherm heating patterns for the grounding point arrangements shown, respectively, in FIGS. 7, 8 and 9.

Operational characteristics of the hyperthermic treatment device of the present invention have been evaluated using phantom bodies comprising truncated cones composed of various mixtures of WHAMO-SUPER STUFF ®, saline, polyethylene powder, and powered aluminum in accordance with formulas developed by the Bioelectromagnetics Laboratory at the University of Washington and as described in Bolanzo, Q., et al., "Attempts to Evaluate the Exposure of Portable Radio Operators at 30MHz," *IEEE Conference of the Vehicular Technology Group, Chicago, Ill.* (1979). The dielectric properties of the phantom material are set forth in TABLE I below along with comparisons to various canine tissue.

TABLE I

| Phantom Mixture | f = 13 MHz | | | f = 20 MHz | | |
| --- | --- | --- | --- | --- | --- | --- |
| | $\epsilon'$ | $\epsilon''$ | $\tau$(ns) | $\epsilon'$ | $\epsilon''$ | $\tau$(ns) |
| 1 | 132.08 | 6.24 | 12.58 | 129.20 | 10.32 | 7.16 |
| 2 | 65.54 | −1.26 | 12.58 | 65.92 | −1.83 | 8.24 |
| 3 | 59.71 | 2.01 | 11.73 | 59.28 | 2.76 | 8.29 |
| dog liver | 73.46 | 1.75 | 11.65 | 73.39 | 2.43 | 8.40 |
| dog skeletal muscle | 47.61 | 1.04 | 11.65 | 47.48 | 2.00 | 6.06 |
| dog lung | 48.00 | 1.36 | 11.03 | 47.95 | 1.90 | 7.90 |
| dog small intestine | 176.07 | 31.08 | 12.58 | 169.20 | 46.18 | 8.24 |
| dog spleen | 89.81 | 2.77 | 11.65 | 89.68 | 3.84 | 8.40 |
| dog heart | 71.24 | 1.46 | 11.73 | 71.21 | 2.07 | 8.29 | f = frequency
$\epsilon'$ = real permittivity
$\epsilon''$ = imaginary permittivity
$\tau$ = dielectric relaxation time (ns)
Mixture
1. WHAMO SUPER STUFF ®, saline, powered aluminum
2. WHAMO SUPER STUFF ®, saline
3. WHAMO SUPER STUFF ®, saline, polyethylene powder Phantom bodies used in experimentation with the device measure 20 cm in height by 20-25 cm in diameter. Accordingly, the phantom bodies have cross-sectional dimensions roughly equivalent to the thorax or abdomen of a medium-sized child or a small adult. Temperature monitoring during heating of phantom bodies uses a non-field perturbing Luxtron FLUOROPTIC ® 1000 V temperature probe available from Luxtron Corporation of Mountainview, Calif. Temperature isobars are obtained at the midplane by use of thermally-sensitive Parker Liquid Crystal Paper obtained from Edmond Scientific of Barrington, N.J.

In operation, the device is first tuned in a 13-20 MHz range without loading and in a given spatial configuration of the RF elements using the impedance matcher 36 and the tuning capacitors in the tuner/phase shifter networks associated with the inductor rings and capacitor plates. Then, a field probe consisting of two orthogonally oriented loops connected via diodes to separate milliameters is used to map relative magnetic and electric field intensity in different regions of space within the zone of RF energy. These patterns are used to estimate optimal positions for placement of bodies within the zone of focal radiofrequency. fields. Next, a body is placed in position and the device is then impedance matched to the load and fine adjustments of the field pattern are made using the tuning capacitors in the tuner/phase shifter networks associated with the inductor rings and capacitor plates.

In experiments with phantom bodies, power was applied to the field generators until the desired temperature was reached, as indicated by the temperature probe, whereupon the phantom was removed, bisected and the liquid crystal paper applied at the surface of the midplane of the phantom until a heating pattern is obtained.

Figure 13:
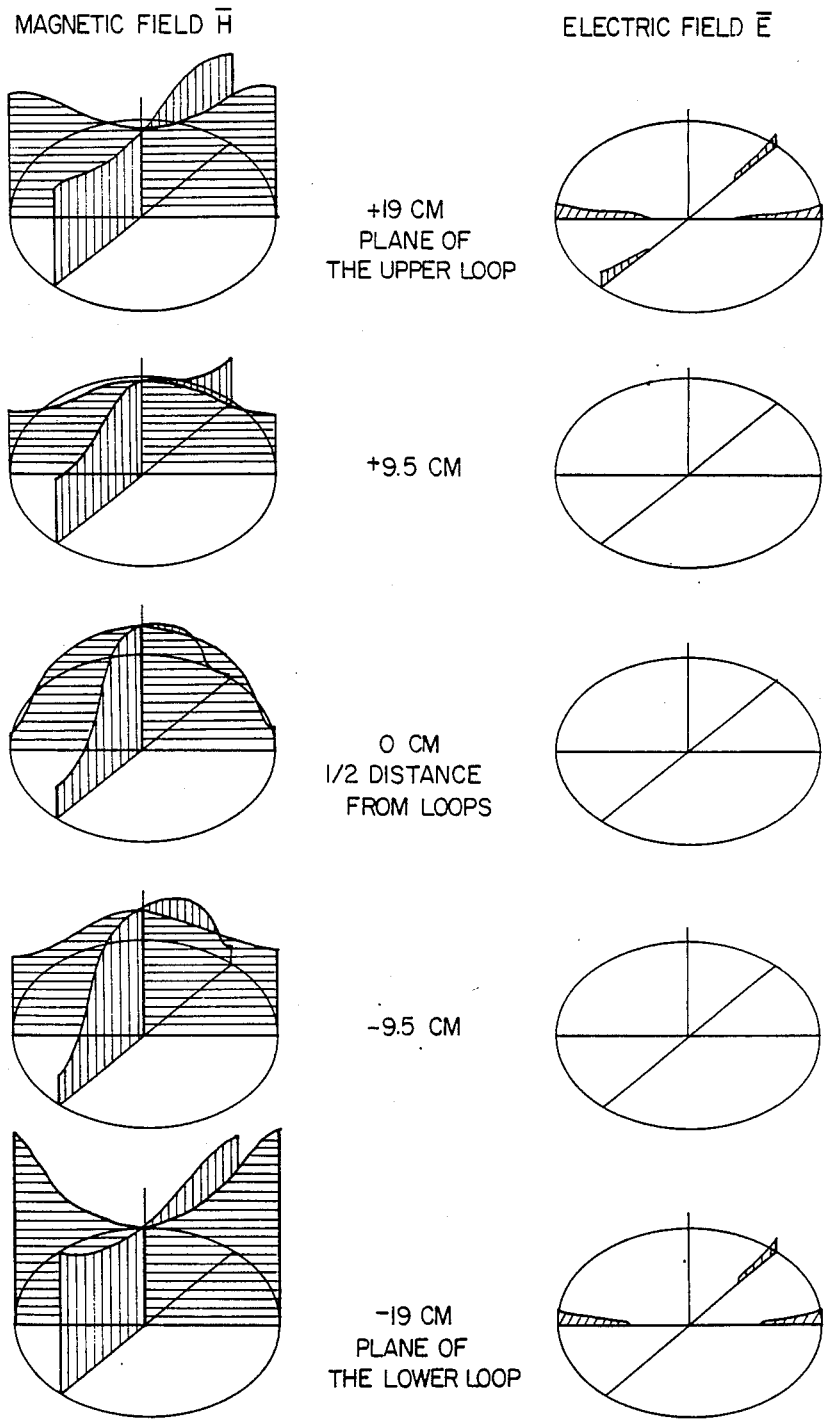
FIG. 13 is a series of diagrams of $\overline{H}$ field and $\overline{E}$ field characteristics of the device of FIG. 1 when the paired inductor rings are in a Helmholtz configuration.
Figure 14:
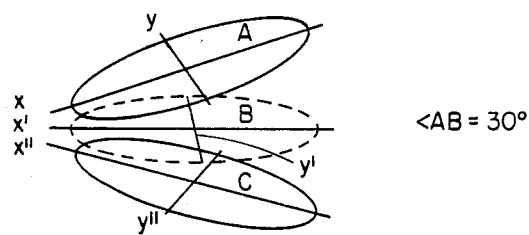
FIG. 14 is a diagram of a wedged configuration of the inductor rings in the device of FIG. 1.
Figure 15:
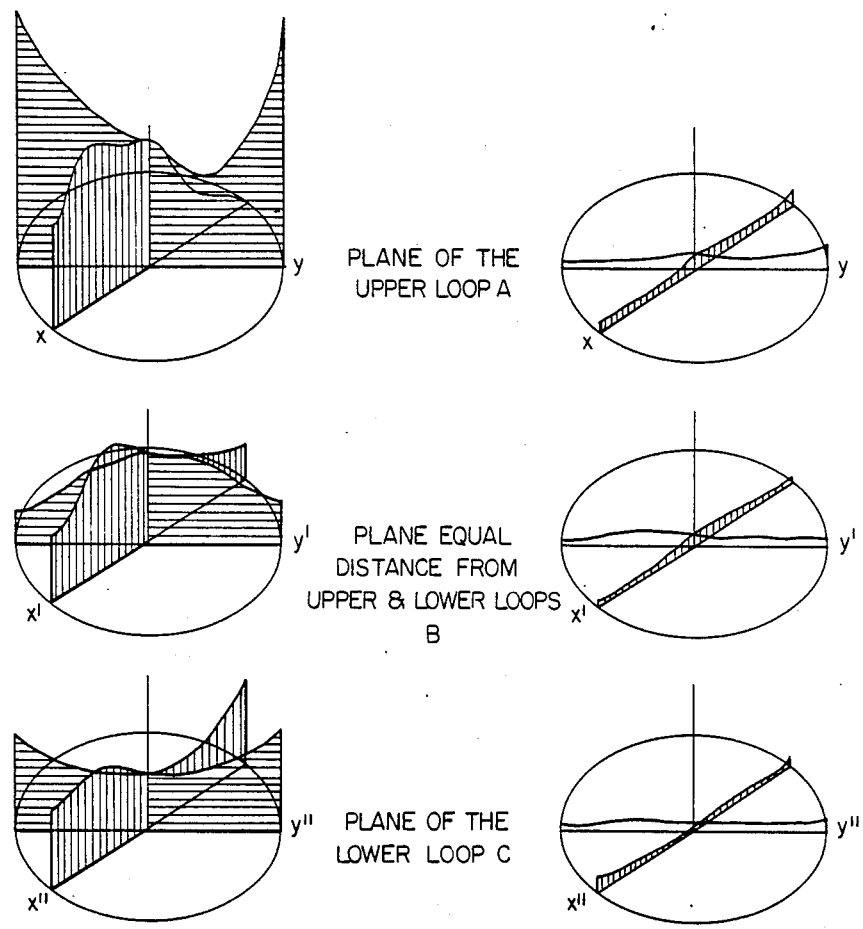
FIG. 15 is a series of diagrams of $\overline{H}$ field and $\overline{E}$ field characteristics of the device of FIG. 1 when the paired inductor rings are in the wedged configuration shown in FIG. 14.

The experimental results indicate that when the inductor rings are positioned in a standard Helmholtz configuration, the relative magnetic and electric fields measured in various planes either within or between the inductor rings are as illustrated in FIG. 13. In the midplane between the inductor rings, the $\overline{H}$ field has a symmetrical bell-shaped distribution with the maximum intensity in the center of the plane. Rotation of the inductor rings into a wedged configuration as shown in FIG. 14 produces an asymmetrical $\overline{H}$ field distribution in the midplane as shown in FIG. 15. As indicated in FIG. 15, the point of maximum intensity shifts off center. Also, it is observed that the inductor rings are associated with relatively weak electric fields $\overline{E}$.

Figure 18:
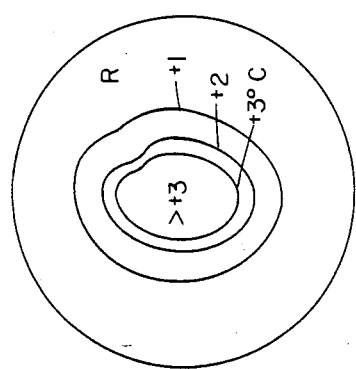
FIG. 18 is a diagram of the heating pattern produced at midplane depth within a spherical phantom placed radially outward of the nonrotated vertical axis of the inductor rings and midway between them, by the inductor rings when in a wedged configuration and when a grounding point is introduced into the volume of the phantom.
Figure 17:
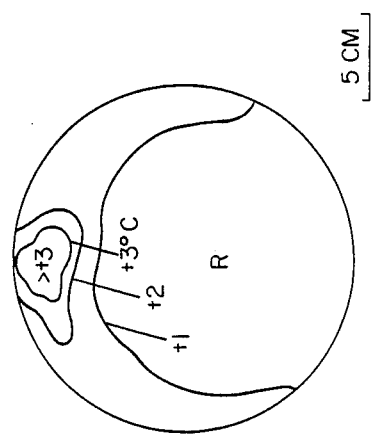
FIG. 17 is a diagram of the heating pattern produced at midplane depth within a spherical phantom placed radially outward of the nonrotated vertical axis of the inductor rings and midway between them, by the inductor rings when in a wedged configuration.
Figure 16:
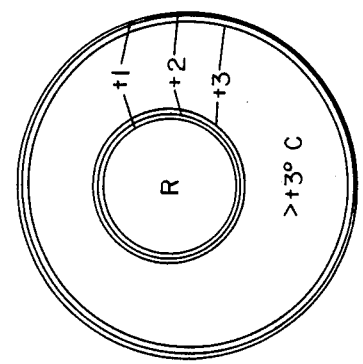
FIG. 16 is a diagram of the heating pattern produced on midplane depth within a truncated cone phantom placed on a position concentric with the vertical axis of the inductor rings and midway between them, by the inductor rings when in a Helmholtz configuration.

In heating experiments with the inductor rings arranged in a paired Helmholtz configuration and truncated cone phantom bodies placed in a position concentric with the vertical axis of the inductor rings and midway between them, a toroidal heating distribution was produced at midplane depth with maximum heat deposition just under the object boundary and a cold central area. This is illustrated in the diagram of FIG. 16. But, with the rings rotated into a wedged configuration and the eddy current field focused using the capacitor plates, and also with the phantom moved radially outward in the midplane along a direction of increasing magnetic and eddy current gradients, eccentrically located focal heating patterns were produced at midplane depth in both truncated cone and spherical phantoms. This is illustrated in the diagrams of FIGS. 17 and 18. However, there was infrequent heating in the central axis of the phantom. Addition of a grounding point introduced into the volume of the phantom to provide a current drain focused eddy currents into the central axis of the phantom and resulted in large (greater than 6 cm) precisely-focused hot spots in the central axis region. FIG. 18 illustrates such a result.

The operational characteristics of the device and the experimental results obtained from the heating of phantom bodies suggests that the device permits sufficient control of induced eddy currents to produce a variety of regionally focused heating patterns at depths suitable for treatment of tumors in the CNS, abdomen, thorax, or pelvis. Use of the device in such treatment is diagrammed in FIGS. 19, 20 and 21.

Figure 19:
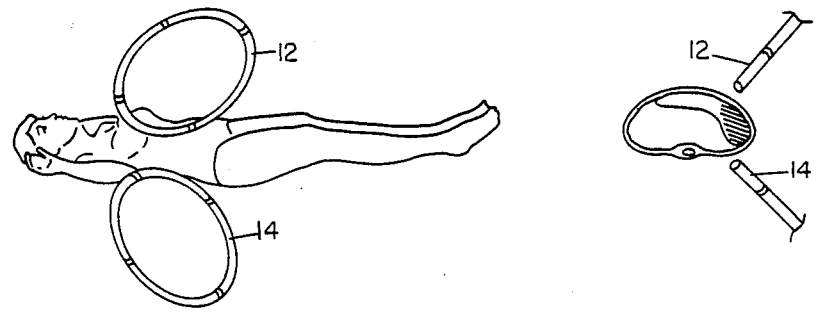
FIG. 19 is an illustrative diagram showing use of the device of FIG. 1 in hyperthermic treatment of a patient wherein the inductor rings are oriented in a wedged configuration.

FIG. 19, a patient is shown disposed between inductor rings 12 and 14, which are oriented in a wedge configuration. Also shown in FIG. 19 is a cross-sectional view of the patient and the positioning of the patient relative to the inductor rings.

Figure 20:
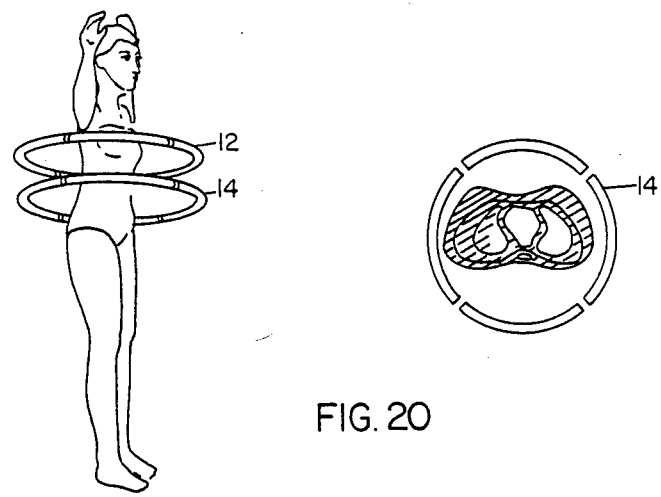
FIG. 20 is an illustrative diagram showing use of the device of FIG. 1 in hyperthermic treatment of a patient wherein the inductor rings are in a Helmholtz configuration and the patient is placed centrally of the rings.

FIG. 20 illustrates a patient placed to be encircled by the upper and lower inductor rings.

Figure 21:
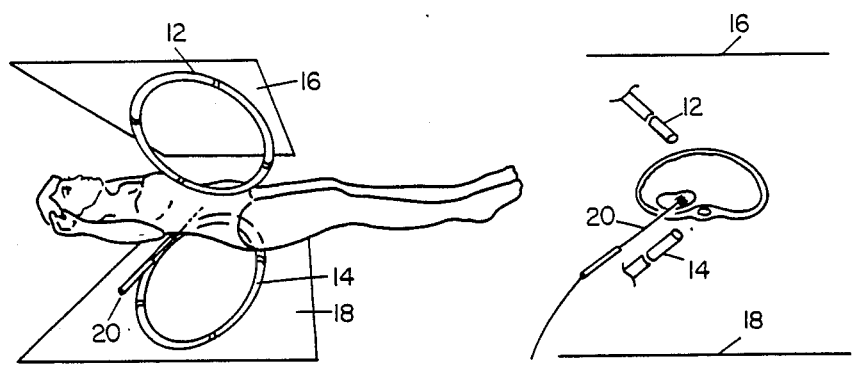
FIG. 21 is an illustrative diagram showing use of the device of FIG. 1 in hyperthermic treatment of a patient wherein an invasive ground probe is utilized.

Finally, FIG. 21 shows a patient disposed between upper and lower inductor rings 12 and 14 and capacitor plates 16 and 18. Further, in FIG. 21, an invasive probe 20 is used as a grounding point. As indicated in the cross-sectional view of FIG. 21, ground probe 20 is introduced into the patient and the tip positioned in the area where heating is to be focused. Placement of an invasive ground probe may be made under computer tomography scan guidance, or with nuclear magnetic resonance imaging.

The foregoing description has been directed to particular preferred embodiments of the present invention for purposes of explanation and illustration. It will be apparent, however, to those skilled in the art that many modifications and changes may in the apparatus may be made. It is the Applicants' intention in the following claims to cover all equivalent modifications and variations as fall within the scope of the invention.

What is claimed is:

1. Apparatus for producing regionally-focused hyperthermia in a body, comprising:
    a radiofrequency electric field generator;
    a radiofrequency magnetic field generator including first and second inductor rings in a paired arrangement;
    said electric field and magnetic field generators, for irradiating a body with electromagnetic radiation to induce eddy currents therein that produce heating of the body; and
    a movable grounding point for disposition within the electromagnetic radiation, for focusing the eddy currents to produce heating at a predetermined region within the body.

2. The apparatus of claim 1 further comprising:
    means for shifting the magnetic field vector direction and intensity in the region of space between the rings.

3. The apparatus of claim 1 further comprising:
    means for independently adjusting the phase of the RF field generated by each inductor ring to thereby alter the resultant $\overline{H}$ field between the inductor rings.

4. The apparatus of claim 1 wherein said RF electric field generator comprises a pair of capacitor plates.

5. The apparatus of claim 4 wherein both of said inductor rings are positioned between said capacitor plates.

6. The apparatus of claim 1 further comprising:
    means for adjusting the spatial orientation of each of said inductor rings.

7. The apparatus of claim 6 wherein said inductor ring orientation adjusting means provides for rotation of each ring about an axis lying in the plane of the ring.

8. The apparatus of claim 1 further comprising:
    means for monitoring the current flowing through the grounding point.

9. The apparatus of claim 1 wherein the grounding point comprises an invasive probe for insertion within the body.

10. The apparatus of claim 9 wherein said probe comprises:
    an elongated rod; and
    an insulating sheath on said rod,
    said sheath exposing the tip of the rod.

11. The apparatus of claim 9 further comprising:
    a ground plane for disposition externally of the body to be heated, said ground plane being selectively connectable to ground potential.

12. The apparatus of claim 1 wherein the grounding point comprises:
    a pair of invasive probes for insertion within the body, and
    a switch for alternately connecting the probes to ground potential.

13. The apparatus of claim 1 wherein the grounding point comprises:
    a grounded plane for disposition externally of the body to be heated.

14. The apparatus of claim 13 further comprising:
    second and third ground planes for disposition externally of the body and on opposite sides thereof; and
    a switch for alternately connecting the planes of ground potential.

15. Apparatus for producing regionally-focused hyperthermia in a body, comprising:
    a radiofrequency magnetic field generator, for producing an asymmetrical magnetic field gradient in a horizontal plane through a body and induce eddy currents therein to cause heating of the body; and
    a radiofrequency electric field generator, for producing an electric field to cancel certain eddy currents and for focusing the eddy current heating to a particular location within the body.

16. The apparatus of claim 15 further comprising:
    a movable grounding point for further focusing the induced eddy currents to a predetermined location within the body.

17. The apparatus of claim 15 wherein said RF magnetic field generator comprises a pair of inductor rings disposed adjacent one another.

18. The apparatus of claim 15 wherein said RF electric field generator comprises a pair of capacitor plates.

19. The apparatus of claim 15 further comprising:
    means for shifting the magnetic field gradient in the horizontal plane.

20. The apparatus of claim 17 further comprising:
    means for independently adjusting the phase of the RF field generated by each inductor ring to thereby alter the resultant $\overline{H}$ field between the inductor rings.

21. The apparatus of claim 17 further comprising:
    means for adjusting the spatial orientation of each of the inductor rings.

22. Apparatus for producing regionally-focused hyperthermia in a body comprising:
    a frame having vertical sidewalls;
    upper and lower capacitor plates mounted in said frame;
    upper and lower inductor rings mounted in said frame between said capacitor plates;
    each inductor ring being mounted for rotation about a horizontal axis in the plane of the ring and mounted for vertical movement;
    means for adjusting the spatial orientation of said upper inductor ring;
    means for adjusting the spatial orientation of said lower inductor ring;
    a source of radiofrequency electrical power coupled to said capacitor plates and to both of said inductor rings, for producing an electric field between the capacitor plates and for driving the inductor rings to produce a resultant magnetic field;
    said driven inductor rings producing an asymmetical magnetic field gradient in a horizontal plane through a body irradiated by the resultant magnetic field that induces eddy currents in the body and causes heating of the body; and
    means for adjusting the phase of the RF field generated by each inductor ring to alter the resultant field between the rings and focus the induced eddy currents to a predetermined location within the body.

23. The apparatus of claim 22 further comprising:
    a movable grounding point for disposition within the magnetic field, for focusing the induced eddy currents to produce heating at a predetermined location within the body.

24. The apparatus of claim 23 wherein the grounding point comprises an invasive probe for insertion within the body.

25. The apparatus of claim 24 wherein the probe comprises:
    an elongated rod of electrically conductive material; and
    an insulating sheath on said rod,
    said sheath exposing the tip of the rod.

* * * * *